United States Patent [19]

Brazhnikov et al.

[11] 3,958,942
[45] May 25, 1976

[54] ANALYZER FOR DETERMINATION OF DOUBLE BONDS

[76] Inventors: Evgeny Mikhailovich Brazhnikov, Profsojuznaya ulitsa, 109, kv. 176; Viktor Ivanovich Gerbich, ulitsa Dovatora, 1/28, kv. 54; Igor Vladimirovich Krinsky, ulitsa Nametkina, 13, korpus 2, kv. 40; Dmitry Mitrofanovich Lisitsyn, Buturskaya ulitsa, 2/18, kv. 126; Vladimir Fedorovich Moskvin, Leninsky prospekt, 60/2, kv. 506; Stanislav Dmitrievich Razumovsky, Vorobievskoe shosse, 11, kv. 68; Evgeny Kalikstovich Russian, Vorobievskoe shosse, 11, kv. 62; Gennady Romanovich Truonikov, ulitsa Vavilova, 55/7, kv. 102; Vladimir Ivanovich Chernykh, Perekonskaya ulitsa, 14, korpus 2, kv. 44; Andrei Stepanovich Shalomeev, Lenisky prospekt, 37a, kv. 144, all of Moscow, U.S.S.R.; Nikolai Mikhailovich Chirkov, deceased, late of Moscow, U.S.S.R.; by Mikhail Nikolaevich Chirkov, administrator, ulitsa Vavilova, 55/7, kv. 6, Moscow, U.S.S.R.

[22] Filed: Feb. 21, 1975

[21] Appl. No.: 551,781

Related U.S. Application Data

[63] Continuation of Ser. No. 451,299, March 14, 1974, abandoned.

[52] U.S. Cl. .............................. 23/253 R; 250/373
[51] Int. Cl.² .......................... G01J 1/18; G01N 21/26
[58] Field of Search ................ 23/253 R, 230 R; 250/373

[56] References Cited

UNITED STATES PATENTS

| | | | |
|---|---|---|---|
| 2,878,388 | 3/1959 | Bergson | 250/373 |
| 3,384,746 | 5/1968 | Benz et al. | 250/373 |
| 3,505,524 | 4/1970 | Hjerten | 250/373 |

OTHER PUBLICATIONS

Kiffer et al., Anal. Chem. 24, 1796 (1952).
Smits et al., Anal. Chem. 44, 1688 (1972).

*Primary Examiner*—Robert M. Reese
*Attorney, Agent, or Firm*—Holman & Stern

[57] ABSTRACT

An analyser for the determination of double bonds in organic compounds comprises a reactor containing a compound to be tested through which passes an ozone-oxygen or ozone-air mixture. The gas outlet of the reactor is connected to a measuring cell which is mounted between a source and receiver of ultraviolet radiation, with the receiver being connected to the input of an integrating unit which is adapted to measure the area of a figure described by a time-dependent electric signal, which area is directly proportional to the number of double bonds in the compound being tested.

12 Claims, 6 Drawing Figures

ANALYZER FOR DETERMINATION OF DOUBLE BONDS

The invention relates to analytical instruments, and more specifically to an analyzer for the determination of double bonds in organic compounds to be used mainly in research work for determining the number of double bonds in monomers for synthetic rubber and plastics, polymeric and oligomeric products of various types, such as aromatics, oils, greases, products of biological origin, as well as in industries for monitoring chemical production processes (polymerization, oil and fuel production, hydration and dehydration, pyrolisis, cracking, etc.).

At present the determination of double bonds in organic compounds is performed manually. A solution with a known content of a reactant (iodine, bromine) is introduced into a reactor containing a solution of a compound to be tested. The solution is allowed to stay for 4–8 hours with the subsequent titration of the unreacted reactant in the presence of a colour indicator. The content of double bonds is determined on the basis of a change in the coulour of the indicator.

This method for the determination of double bonds is rather insensitive and time-consuming.

It is an object of the invention to provide an analyser for the determination of double bonds in organic compounds, which ensure highly sensitive measurements in a short time, with the final result being obtained in the form of an electric signal.

This object is accomplished by the fact that an analyser for the determination of double bonds in organic compounds which are introduced into a reactor thereof, according to the invention, comprises a source of ozone-oxygen or an ozone-air mixture which is passed through the reactor together with the organic compound being tested, a source of ultraviolet radiation and a receiver of ultraviolet radiation, a means for controlling the flux of the ultraviolet radiation and a measuring cell connected to the gas outlet of the reactor, which are mounted in the path of the ultraviolet radiation in the direction of the flux, so that a change in the ozone concentration in the cell results in a proportional change in an electric signal at the output of the ultraviolet radiation receiver. An integrating unit is also provided which is electrically coupled with the receiver, which measures the area of a figure described by the time-dependent electric signal, said area being directly proportional to the number of double bonds in the organic compound being tested.

The analyser is preferably provided with an additional means for controlling the flux of ultraviolet radiation and an additional receiver of ultraviolet radiation which are located in the path of this radiation not extending through the measuring cell, with the additional receiver being connected to a means for measuring the area of the electric signal in a differential relation to the receiver.

It is expedient that the source of ozone-oxygen or ozone-air mixture comprise an ozonizer using a silent discharge between its electrodes through a glass tube.

It is advantageous to use an ultraviolet radiation source comprising a high-frequency low-pressure mercury lamp.

The receivers of ultraviolet radiation preferably comprise photoemissive cells.

It is expedient that the integrating unit comprise a recording potentiometer, a voltage-pulse frequency converter connected to the output of the potentiometer, a discriminator connected to the input of the potentiometer, and a pulse counter so that in determining double bonds on the basis of the time during which the electric signal entering the discriminator is above a predetermined level, the input of the counter is connected to the input of the discriminator, while in determining double bonds on the basis of the area of a figure described by the potentiometer, the input of the counter is connected to the output of the converter.

It is also advantageous that the voltage-pulse frequency converter comprise a blocking oscillator with a variable threshold value which ensures the actuation of the counter upon the achievement of a predetermined magnitude of the signal entering the potentiometer.

The analyzer for the determination of double bonds according to the invention has high sensitivity and accuracy of measurement and considerably reduces the measurement time. The analyser enables the final measurement result to be obtained in the form of an electric signal.

The invention will now be described with reference to specific embodiments thereof illustrated in the accompanying drawings, in which.

Figure 1:
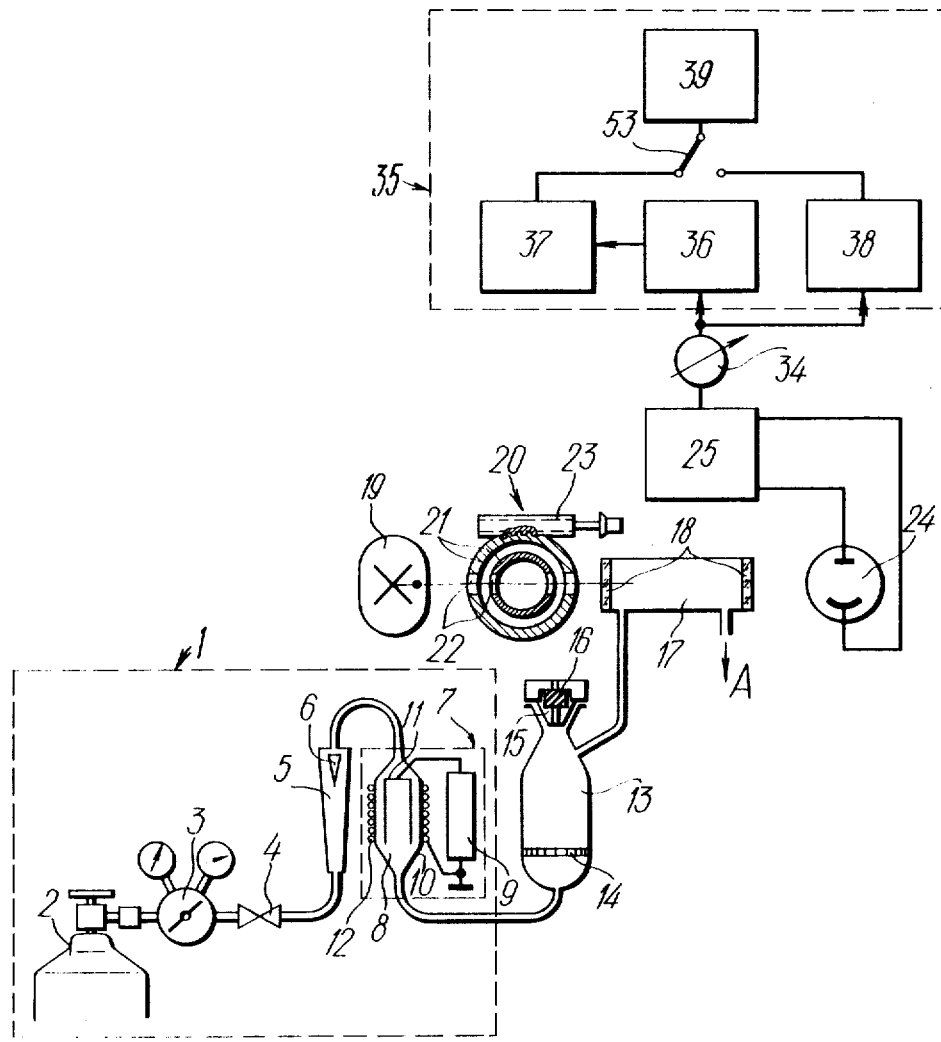
FIG. 1 shows a general diagrammatic view of the first embodiment of the analyser for the determination of double bonds in organic compounds according to the invention.

The analyser for the determination of double bonds according to the invention comprises a source 1 of an ozone-oxygen mixture (FIG. 1) including a bottle 2 filled with oxygen and having a pressure reducer 3. The pressure reducer 3 is connected with a fine adjustment valve 4 by means of a conduit. Mounted at the outlet of the valve 4 is a float-type flow meter 5. The float-type flow meter 5 comprises a conical glass tube. A float 6 is positioned in the tube so that the position of the float determines the flow rate of the working gas. The outlet of the float-type flow meter 5 is connected to the inlet of an ozone generator 7. The ozone generator 7 comprises an ozonizer 8 and a power supply source 9. The ozonizer 8 embodies a glass tube 10. Metallic conductors disposed in the tube 10 are interconnected with their ends so as to form an internal electrode 11 of the ozonizer 8. The external electrode 12 comprises a metallic braiding fitted on the glass tube 10 and is connected to an earthed high-voltage terminal of the high-voltage power supply source 9 of the ozonizer 8, and the internal electrode is connected to a non-earthed terminal.

The gas outlet of the ozonizer 8 is connected to the gas inlet of a reactor 13. In this embodiment the reactor comprises a bubbling reactor in the form of a vessel having a bottom wall comprising a porous glass plate 14. The ozone-oxygen mixture is introduced beneath porous plate 14 which is used as an gas dispersing device. The upper portion of the reactor 13 is filled with a solvent and a compound to be tested which in one example are carbon tetrachloride and octene-1, The upper portion of the reactor is provided with means 15 for the introduction of the compound being tested without affecting the tight seal of the reactor 13.

Means 15 comprises a plug having a removable soft membrane 16 which is chemically resistant relative to oxygen, ozone and the organic solvents.

The gas inlet of the reactor 13 is connected to the inlet of a measuring cell 17.

The measuring cell 17 comprises a metallic tube having the end walls thereof provided with quartz windows which are transparent for ultraviolet radiation. The measuring cell 17 is mounted in the path of the ultraviolet radiation generated by a source of ultraviolet radiation 19.

In this embodiment of the analyser the source of ultraviolet radiation 19 comprises a high-frequency low-pressure mercury lamp with a maximum radiation intensity of 254 nm. The lamp is supplied from a stabilized high-frequency power supply source (not shown in the drawing). Mounted in the path of ultraviolet radiation between the source 19 and the measuring cell 17, is means 20 for controlling the flux of the ultraviolet radiation. Means 20 comprises an adjustable optical slit. The slit is made in the form of two coaxial hollow cylinders 21 having coaxial through holes 22 in their peripheral walls, with the flux of the ultraviolet radiation passing through these holes. One of the cylinders 21 is rigidly secured to the housing of the analyser (not shown in the drawing) and the other is movable by means of a worm transmission gear 23.

A receiver for the ultraviolet radiation 24 is mounted at the output of the measuring cell 17. In this embodiment of the analyser the receiver of ultraviolet radiation 24 comprises a vacuum photoemissive cell having a maximum sensitivity of 254 nm. which is connected to a DC amplifier 25 comprising two balanced amplifier stages. The first stage 26 (FIG. 2) of the amplifier 25 (FIG. 1) comprises a twin triode 27 (FIG. 2) having resistors 28 as the anode load. A resistor 29 is a common cathode load of the triode 27. A resistor 30 is inserted in the grid circuit of one triode, and a reference voltage source 31 and a resistor 32, which constitutes a reference voltage divider together with the resistor 30, are connected in parallel with the resistor 30. A resistor 33 inserted in the grid circuit of the other triode comprises a load for the receiver 24 which is connected between the grid of this triode and the junction of the resistors 29 and 20.

Figure 2:
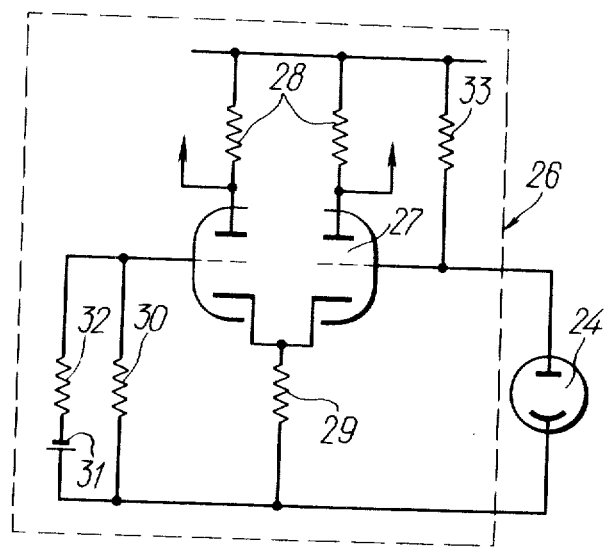
FIG. 2 shows a wiring diagram of the first stage of a DC amplifier for the first embodiment of the analyser according to the invention.

The first and second stages of the DC amplifier 25 (FIG. 1) are coupled in accordance to a known diagram by using an attenuator (not shown in the drawing) which receives the signals from the output of the first stage 26 (FIG. 2) as shown by arrows. An indicating microammeter 34 is connected across the output of the amplifier 25 (FIG. 1). The output of the amplifier 25 is connected to the input of an integrating unit 35.

In this embodiment of the analyser, the integrating unit 35 comprises an automataic recording potentiometer 36, a voltage-pulse frequency converter 37, a discriminator 38 and a pulse counter 39. The input of the unit 35 is at the same time the input of the automatic recording potentiometer 36 and the discriminator 38. The analyser incorporates a modified automatic recording potentiometer 36. An additional precision variable wire resistor 42 is mounted on a shaft 40 (FIG. 3) of a rheostate with the resistor 42 being connected to a stablized DC voltage source 43 of the potentiometer 36. A variable resistor 44 for setting the threashold value of the converter 37 (FIG. 1) is connected to the source 43 in series with the resistor 42. The potentiometer 36 also comprises a motor 45 (FIG. 3) driving the shaft 40 and a motor 46 of a tape driving mechanism 47 which is driven by means of a belt transmission 48. The shaft 40 is connected by means of a cable 49 to a pointer 50 of a scale 51. The pointer 50 is concurrently used for recording of the readings on the paper tape 52. The output of the resistor 42 is operatively connected to the input of the voltage-pulse frequency converter 37 (FIG. 1). The voltage converter 37 is made according to a known diagram and comprises a blocking oscillator with variable threshold value.

The discriminator 38 comprises a coincidence circuit with varying levels of discrimination of the signal being measured.

On FIGS. 1 and 7 the shapes of rectangular pulses is conditionally not shown. Used as reference pulses may be sinusoid voltage of industrial frequency which is fed to the discriminator 38.

The reference pulses fed to one of the outputs of the discriminator 38 represent rectangular pulses which are shaped in synchronism with the power supply network. The output of the voltage coverter 37 and discriminator 38 are connected to the input of the pulse counter vis a selector switch 53.

In measuring the number of double bonds on the basis of the area of a figure recorded by the automatic recording potentiometer 36, the input of the pulse counter 39 is connected to the output of the voltage-frequency converter 37. In measuring the number of double bonds on the basis of the width of the figure, the input of the pulse counter 39 is connected to the output of the discriminator 36. The pulse counter 39 used in the analyser comprises a known decimal six-digit counter with a digital display (sf. journal PRIBORY I TEKHNIKA EKSPERIMENTA, Nauka publishers, 1972, No. 1, p. 242).

The analyser for determination of double bonds in organic compounds according to the invention has a high sensitivity relative to the measured value, whereby its field of application can be enlarged. The analyser is also characterized by an improved accuracy of measurements which is due, in particular, to the opportunity of operating without special indicators and with direct measurement of the presence or absence of ozone in the ozone-oxygen mixture so that the resulting measurement is obtained in the form of an electric signal, and yet the analyser is simple in structure and may be modularized.

Another embodiment of the analyser for the determination of double bonds in organic compounds according to the invention is similar to that described hereinabove.

Figure 4:
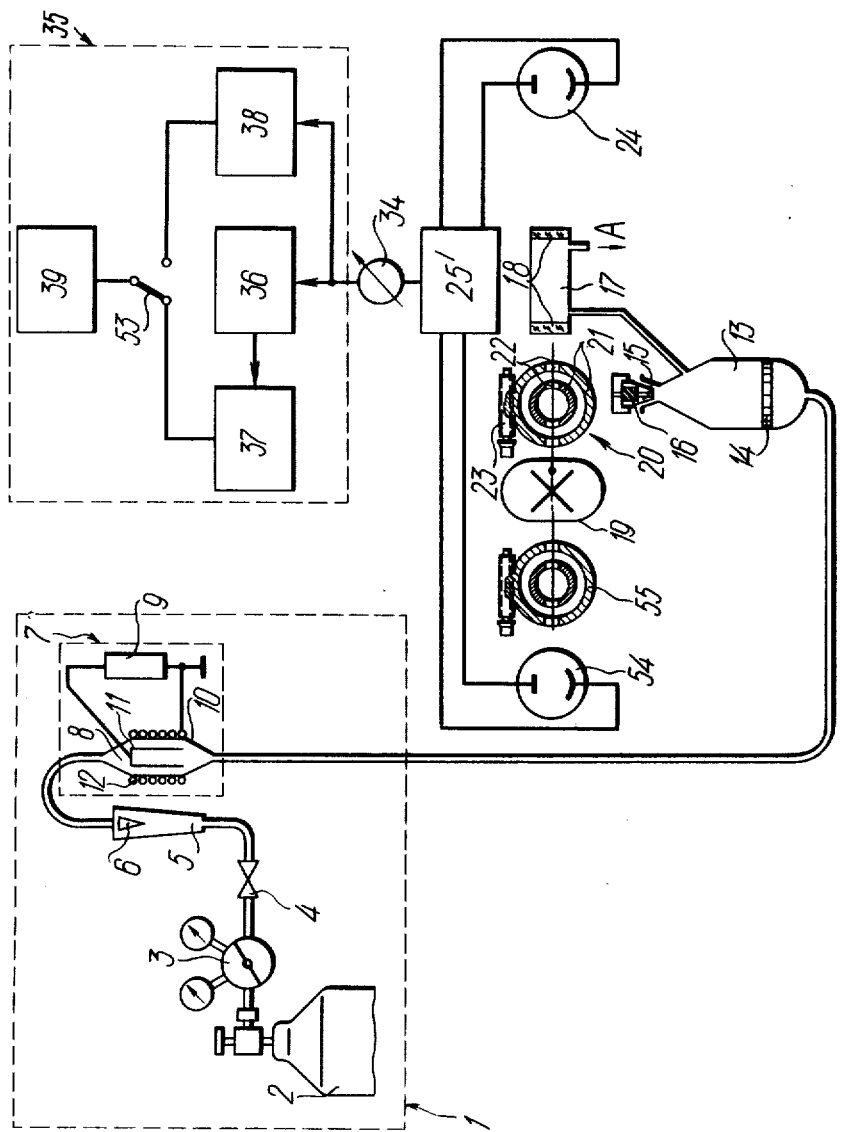
FIG. 4 shows a general diagrammatic view of the second embodiment of the analyser according to the invention.

This embodiment differs in the fact that an additional receiver of the ultraviolet radiation 54 and additional means for controlling the flux of this radiation, which are similar to those described above, are mounted in the path of radiation of the source of ultraviolet radiation 19 (FIG. 4) not extending through the measuring cell 17.

Figure 5:
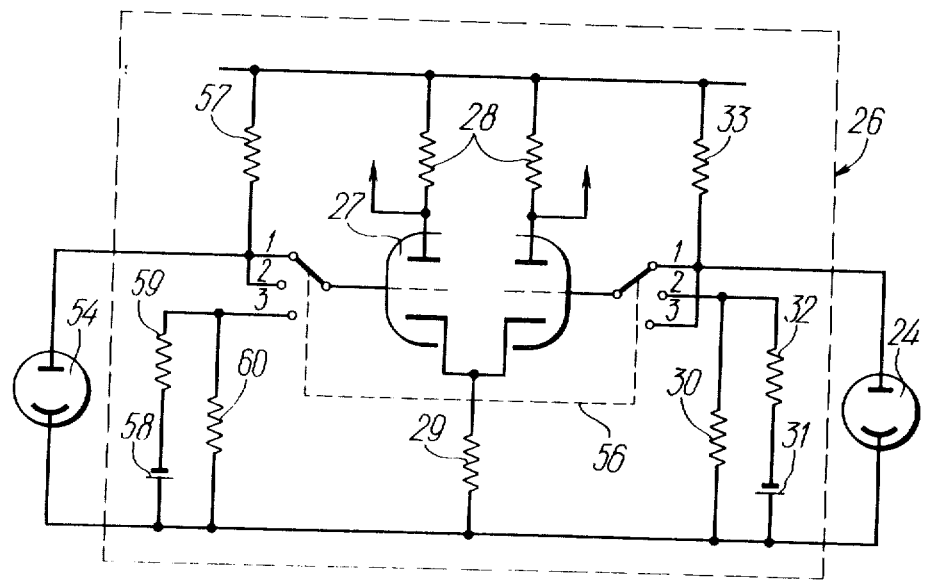
FIG. 5 shows a wiring diagram of the first stage of a DC amplifier for the second embodiment of the analyser according to the invention.

The additional receiver 54 is connected to a DC amplifier 25' in differential relation to the main receiver 24. The first stage 26 (FIG. 5) of the amplifier 25' is additionally provided with a selector switch 56 so that at the first position of the switch the receivers 24 and 54, together with the resistors 33 and 57 comprising their loads, are connected to the grids of the twin troide 27. At the second position of the switch 56 the reference voltage source 31, together with the resistors 30 and 32, is connected to one grid of the triode 27, and the additional receiver 54 and the resistor 57 are connected to the other grid thereof. At the third position of the switch 56 the receiver 24 and the resistor 33 are connected to one grid of the twin triode, and an additional reference voltage source 58 similar to the source 31, as well as resistors 59, 60, which are inserted in the circuit of the source 58 similarly as the resistors 30 and 32 are connected to the other grid.

Figure 3:
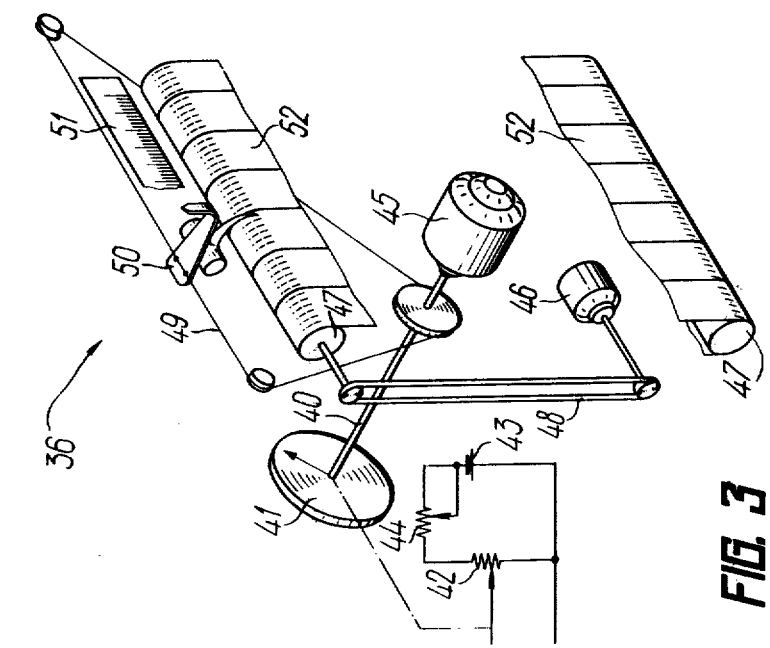
FIG. 3 is a general view of an automatic recording potentiometer of the analyser according to the invention.

The analyser for determination of double bonds in organic compounds functions as follows:

First, the power supply of the analyser is switched on. Oxygen is fed into the gas system of the analyser by means of the pressure reducer 3 (FIG. 1). The desired flow rate of oxygen is adjusted by means of the fine adjustment valve 4 and the flow meter 5. Oxygen is fed from the flow meter 5 into the ozone generator 7, wherefrom ozone-oxygen mixture is fed into the reactor 13, which has been filled with carbon tetrachloride. The oxone oxygen mixture flows from the gas outlet of the reactor 13 into the measuring cell 17 and is then discharged as shown by arrow A. While passing through the measuring cell 17, the ozone absorbs ultraviolet radiation from the source 19. Accordingly, the value of the flux incident upon the receiver of ultraviolet radiation 24 is changed so that the signal at the output of the receiver is also changed. By varying the value of the high voltage at the electrodes 11 and 12 of the ozonizer 6, or by adjusting means 20, and observing the readings of the indicating microammeter 34, or the automatic recording potentiometer 36, the origin of the reading is set up by means of the resistor 44 (FIG. 3). The threshold values of the voltage-pulse frequency converter 37 (FIG. 1) are adjusted accordingly.

Then a known quantity of ocetene-1 is introduced into the reactor 13 through means 15 by using a syringe. An abrupt reduction of the ozone concentration occurs in the reactor 13 due to the fact that ozone adhers to double bonds. Therefore, the ozone content in the ozone-oxygen mixture passing through the measuring cell 17 decreases. Accordingly, the absorption of the ultraviolet radiation passing through the measuring cell 17 and reaching the receiver 24 is also changed. This results in a change in the signal at the input of the DC amplifier 25 and integrating unit 35.

Since an almost complete absorption of ozone takes place in the reactor 13, the automatic potentiometer 36 will reveal a rapid change in the voltage from minimum to maximum value, and it will be in this state until all the double bonds in the octene-1 introduced into the reactor 13 are consumed for reaction with ozone. Then the concentration of ozone in the ozone-oxygen mixture at the outlet of the reactor 13 and in the measuring cell 17 will begin to increase almost up to the original level, so that the pointer 50 (FIG. 3) of the automatic potentiometer 36 will also return to it's initial position. If necessary, by varying the gain of the DC amplifier 25 (FIG. 1) by means of the attenuator, a required sensitivity range of the analyser is adjusted, and a new sample of the compound being tested is introduced. When the signal at the output of the DC amplifier 25 attains the values equal to the adjusted threshold values of the voltage converter 37 and discriminator 38, voltage pulses will appear at the output of the converter 37, with the number of pulses being proportional to the voltage magnitude at the input of the converter 37, while at the output of the discriminator 38, voltage pulses will appear whose number is proportional to the time during which the voltage at the input of the discriminator 38 is above the adjusted threshold value. The respective value is recorded by the pulse counter 39 dependent with which output it is connected to via the selector switch 53.

Figure 6:
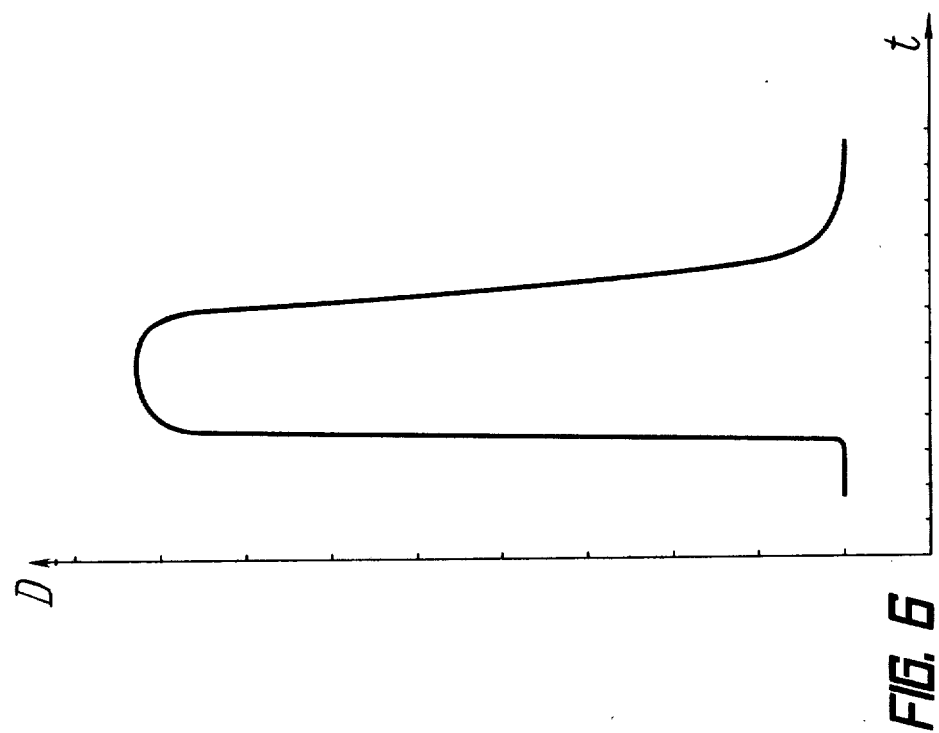
FIG. 6 is a time-dependent diagram of the variation of ozone concentration in the ozone-oxygen mixture obtained in testing octene-1 by using the analyser according to the invention.

For a better understanding of the operation of the analyser FIG. 6 shows a diagram for the variation of ozone concentration in the ozone-oxygen mixture during the analysis of octene-1, wherein time t is plotted on the abscissa and the ozone concentration D is plotted on the ordinates.

The area of a figure below the curve recorded by the recording potentiometer 36 (FIG. 1), or the number of pulses recorded by the pulse counter 39, is directly proportional to the quantity of the absorbed ozone, and hence to the number of double bonds in the compound being tested.

The number of double bonds is obtained by multiplying the number of pulses measured by a proportionality factor which is determined by using a reference sample.

In order to determine the proportionality factor, a known quantity of a reference sample, such as stilbene, is introduced into the reactor 13, and the measurements are conducted as described above.

The proportionality factor is determined on the basis of the number of pulses obtained and the known number of double bonds in stilbene.

In the case where impurities of a solvent or of a compound being tested, as well as in the case where the reaction products (ozonides) react with ozone, the levels of the signals fed from the output of the amplifier 25 before and after the measurement are not equal. The the threshold value of the discriminator 38 or voltage-frequency converter 37 is then adjusted depending upon which output is connected to the pulse counter 39.

The difficulties associated with the stabilization of the intensity of the light flux, and in particular, the ultraviolet flux of the gas-filled lamps are well known. Despite the fact that a low-pressure lamp is used in the analyser as the source 19 of ultraviolet radiation, which is supplied from the stabilized power supply source, the drift of the intensity of the light flux limits the improvement of the sensitivity of the analyser. The sensitivity of the analyser is also limited by the drift of the receiver of ultraviolet radiation 24.

In order to reduce the drift, the analyser is provided, as was mentioned above, with an additional receiver of ultraviolet radiation 54 having at the inlet thereof means 55 for controlling the flux of ultraviolet radiation which is mounted in the path of radiation of the same source not extending through the measuring cell 17, with the receiver being connected to an amplifier 25' in differential relation to the main receiver 24.

The second embodiment of the analyser functions similarly to the first embodiment thereof.

The only difference consists in the fact that prior to the beginning of the operation the operating conditions of the receivers 25 and 54 and of the DC amplifier 25' are adjusted as follows: The selector switch 56 (FIG. 5) is set to the second position, and then means 55 is used (FIG. 4) to set the pointer 50 (FIG. 3) of the potentiometer 36 to the zero point of its scale 51 which will correspond to the equality between the signals of the receiver 54 (FIG. 5) and the source 31, respectively. Then the switch 56 is set to the third position, and the above-described operation is repeated so as to achieve the equality of the signals of the receiver 24 and the source 58, respectively. Then the selector switch 56 is set into the first position, and the measurements are conducted as it was described above for the first embodiment.

The analyser for the determination of double bonds in an organic compound according to the invention operates in the same manner in both the above-described embodiments when using an ozone-air mixture.

The analyser of double bonds in organic compounds according to the invention has high sensitivity, whereby its field of application is considerably enlarged. It enables high accuracy of measurements since the visual determination for the moment of a change in the colour of an indicator is replaced by the measurement of the parameter which is directly proportional to the number of double bonds. The analyser ensures that the results of the analysis be obtained in the form of an electric signal, whereby it may be used for monitoring the production processes performed with changes in the content of double bonds in the product. The analyser according to the invention substantially reduces the time required for an analysis. The simple structure and the compact analyser circuitry enables its modularization.

What is claimed is:

1. An analyser for the determination of double bonds in organic compounds comprising: a reactor containing a compound to be tested having a gas outlet; a source of a gas mixture selected from the group consisting of ozone-oxygen and ozone-air mixtures in communication with said reactor; a measuring cell in communication with said gas outlet of said reactor; a source of ultraviolet radiation, with said measuring cell being mounted in the path of the radiation of said source; a receiver of ultraviolet radiation mounted in the path of ultraviolet radiation of said source, which has passed through said measuring cell; means for controlling the flux of ultraviolet radiation mounted in the path of the radiation between said source and said measuring cell; and an integrating unit operatively connected to said receiver of ultraviolet radiation, said integrating unit measuring the area of a figure described by a time-dependent electric signal which area is directly proportional to the number of double bonds in the organic compound being tested.

2. The analyser according to claim 1, wherein said integrating unit comprises a recording potentiometer operatively connected to said receiver of ultraviolet radiation, a voltage-pulse frequency converter operatively connected to the output of said potentiometer, a discriminator operatively connected to the input of said potentiometer, and a pulse counter, said pulse counter either being operatively connected to the output of said converter in determining double bonds on the basis of the area of a figure described by said potentiometer, or being operatively connected to the output of said discriminator in determining double bonds on the basis of the time during which the electric signal entering said discriminator is above a perdetermined level.

3. An analyser according to claim 2, wherein said voltage-pulse frequency converter comprises a blocking oscillator with variable threshold value which ensures the actuation of said pulse counter upon the achievement of a predetermined magnitude of the signal entering said potentiometer.

4. The analyser according to claim 1, comprising an ozonizer as said source of a gas mixture, said ozonizer comprising a glass tube installed in the gas stream in front of the reactor inlet and electrodes mounted inside and outside said glass tube, said ozonizer using a silent discharge between said electrodes through said glass tube.

5. An analyser according to claim 4, wherein said source of ultraviolet radiation comprises a high-frequency low-pressure mercury lamp.

6. An analyser according to claim 10, wherein said receiver of ultraviolet radiation comprises a photoemissive cell.

7. The analyser according to claim 1, comprising an additional receiver of ultraviolet radiation of said source by-passing said measuring cell and which is operatively connected to said means for measuring the area of the electric signal in a differential relation to said main receiver; additional means for controlling the flux of ultraviolet radiation which is mounted between said source and said additional receiver of ultraviolet radiation.

8. The analyser according to claim 7, wherein said integrating unit comprises a recording potentiometer operatively connected to said receiver of ultraviolet radiation, a voltage-pulse frequency converter operatively connected to the output of said potentiometer, a discriminator operatively connected to the input of said potentiometer, and a pulse counter, said pulse counter either being operatively connected to the output of said converter in determining double bonds on the basis of the area of a figure described by said potentiometer, or being operatively connected to the output of said discriminator in determining double bonds on the basis of the time during which the electric signal entering said discriminator is above a predetermined level.

9. An analyser according to claim 8, wherein said voltage-pulse frequency converter comprises a blocking oscillator with variable threshold value which ensures the actuation of said pulse counter upon the achievement of a predetermined value of the magnitude of the signal entering said potentiometer.

10. The analyser according to claim 7, comprising an ozonizer as said source of a gas mixture, said ozonizer comprising a glass tube installed in the gas stream in front of the reactor inlet and electrodes mounted inside and outside said glass tube, said ozonizer using silent discharge between said electrodes through said glass tube.

11. An analyser according to claim 10, wherein said source of ultraviolet radiation comprises a high-frequency low-pressure mercury lamp.

12. An analyser according to claim 10, wherein said receiver of ultraviolet radiation comprises a photoemissive cell.

* * * * *